US00PP14189P29

(12) United States Plant Patent
Olbricht

(10) Patent No.: US PP14,189 P2
(45) Date of Patent: Sep. 30, 2003

(54) ANGELONIA PLANT NAMED 'ANBLAUZWEI'

(50) Latin Name: *Angelonia gardneri*
Varietal Denomination: 'Anblauzwei'

(75) Inventor: Klaus Olbricht, Dresden (DE)

(73) Assignee: Elsner Pac Jungpflanzen (DE)

( * ) Notice: Subject to any disclaimer, the term of this patent is extended or adjusted under 35 U.S.C. 154(b) by 0 days.

(21) Appl. No.: 10/118,195

(22) Filed: Apr. 8, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Susan B. McCormick
(74) *Attorney, Agent, or Firm*—Webb Ziesenheim Logsdon Orkin & Hanson, P.C.

(57) ABSTRACT

A new and distinct angelonia plant with blue colored flowers with white eye, compact growth and short internodes.

1 Drawing Sheet

Botanical classification: *Angelonia gardneri.*
Varietal denomination: 'Anblauzwei'.

BACKGROUND OF THE INVENTION

The present invention comprises a new and distinct cultivar of *Angelonia gardneri* known by the varietal name 'Anblauzwei.' The new variety was discovered in 2001 in a selective breeding program in Dresden, Germany. The new variety is the result of a combination breeding of violet-blue colored flowered, unnamed, unpatented selections from breeding group 0K-85. Plants of the new variety are single flowering and exhibit a more intense flower color and larger flower size than their heritage. 'Anblauzwei' also exhibits shorter growth than the other seedlings of breeding group OK-85. The new variety was first asexually reproduced by cuttings in Dresden, Germany in 2001. The new variety has been trial and field tested and has been found to retain its distinctive characteristics and remain true to type through successive propagations.

DESCRIPTION OF THE DRAWING

The accompanying photographic drawing illustrates the new variety, with the color being as nearly true as is possible with color illustrations of this type.

DESCRIPTION OF THE PLANT

The following detailed description sets forth the characteristics of the new cultivar. The data which defines these characteristics were collected on a 9 month old plant grown in pots indoors and outdoors during Spring and Summer and in greenhouses in Autumn. The color readings were taken indoors under natural light. Color references are primarily to the R.H.S. Colour Chart of The Royal Horticultural Society of London.

PLANT

Form: Erect.
Height from media surface to top of foliage: 40–60 cm.
Height from media surface to top of racemose: 40–60 cm.
Growth: Erect, good branching.
Strength: Does not require artificial support.

Roots:
*Time to develop.*—2.5–3 weeks.
*Color.*—Whitish and 130D.
Leaves: Opposite, 5.5–6 cm long, 1.5 cm wide.
*Shape.*—Lanceolate overall with pointed base and pointed apex.
*Margin.*—Serrated.
*Texture.*—Smooth, few hairs.
*Color.*—Upper surface: 139A. Lower surface: 137B.
Ribs and veins: Net-like, 138B.
Petioles: 0.2 cm long, 138B.
Stem/branches: 137C.
*Overall stem lengths.*—50 cm.
*Internode lengths.*—1.0–2.0 cm.
*Lateral branch length.*—5–7 cm.

THE BUD

At stage of opening, but still closed: Racemose, spherical individual bud, 138C, 4–6 cm long cluster, 4–5 mm bud.

INFLORESCENCE

Blooming habit: Single, continuous flowering.
Size of fully open bloom: 6 cm across.
Borne: 5 petals grown together, one flower on pedicel, pedicel on stem.
Flowers:
*Form.*—Zygomorph.
*Presence.*—1–2 flowers per leaf axil.
*Size.*—3.0–3.5 cm wide; 1.0 cm deep.
*Petals.*—Upper surface 83A; Lower surface 83C; Eye 145D appears dark blue from a distance; also, traces of 145D on the petal surface. Size: 1.2 cm long, 1.7 cm wide. Shape: Round apex, corolla-like base. Margin: Undulating, smooth. Texture: Velvety, hairy.
Sepals:
*Number.*—5 per infloresence.
*Shape.*—Overall: Round. Apex: Round. Base: Round, grown together.
*Color.*—Upper surface.—138B. Lower surface.—137B.
*Size.*—Length: 0.4 cm. Width: 0.3 cm.
Petaloids: Absent.
Peduncle: Absent.
Pedicel: 1.4 cm long, 184D.

Disease/pest resistance: No unusual susceptibility to diseases or pests noted to date.
Lasting quality: Plants last until first frost.

REPRODUCTIVE ORGANS

Stamens: Not present; anthers grow directly on the petal.
Anthers: 3 mm long.
Filaments: 2–3 mm long, 85D with abundant pollen colored 11D.
Pistils: 1, 1 mm long, 130D.
*Style.*—3–4 mm long, 130D.
*Ovaries.*—Superior, smooth, 1–2 mm long, 78B.
Fruit: If present, capsule 0.5 cm long with 50–100 seeds, 0.05 cm long, 163D.

GENERAL CHARACTERISTICS

1. Compact growth.

2. Intense blue color.

3. Short internodes.

4. White eye.

5. No cleaning necessary.

I claim:

1. A new and distinct variety of angelonia plant substantially as shown and described.

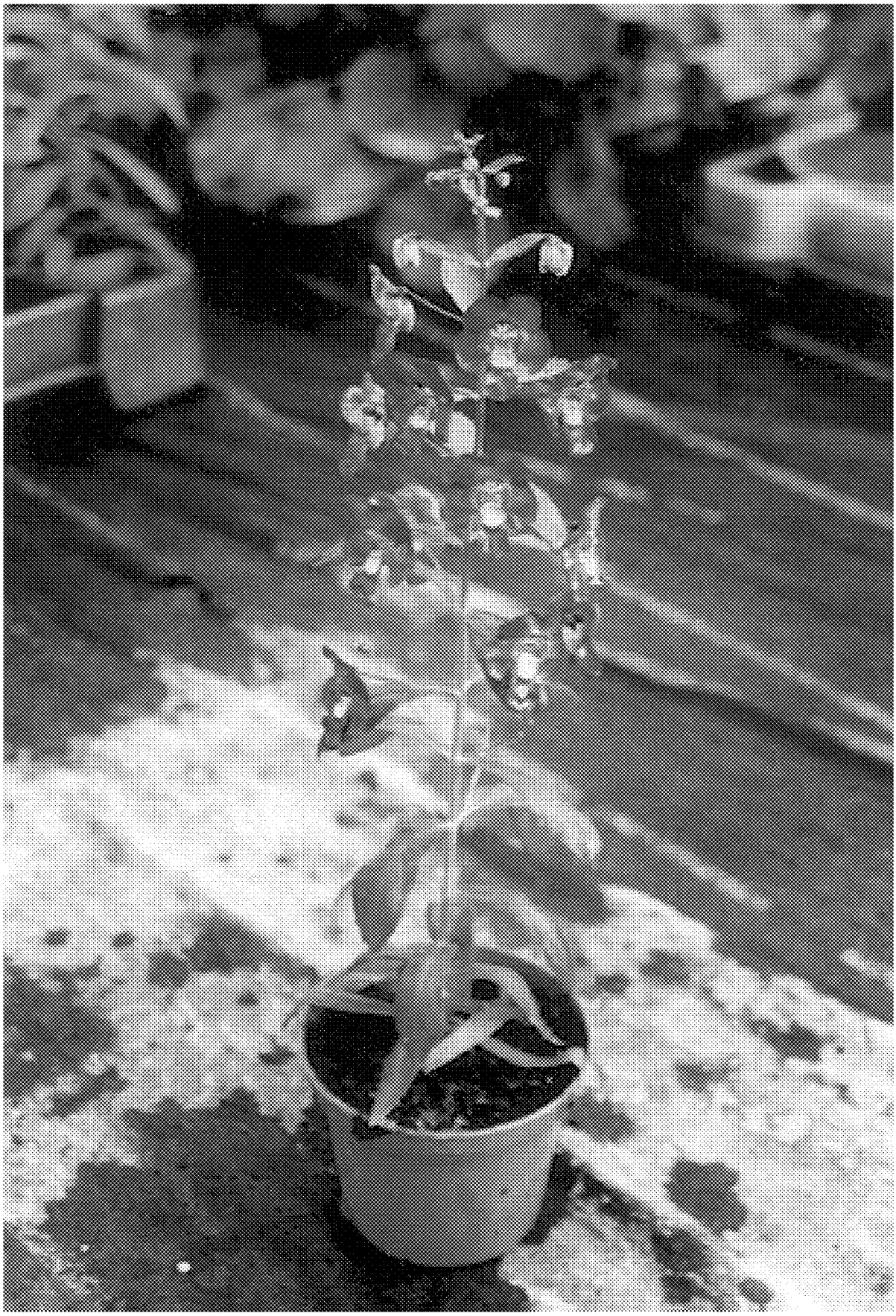

* * * * *